United States Patent
Lindh et al.

(10) Patent No.: US 6,908,444 B2
(45) Date of Patent: Jun. 21, 2005

(54) USE OF A HEATABLE MAT FOR MANUFACTURING AN ORTHOTIC DEVICE

(75) Inventors: Leif Lindh, Danderyd (SE); Kjell Lindh, Lidingö (SE)

(73) Assignee: Danderyds Biotech Innovation AB, Danderyd (SE)

(*) Notice: Subject to any disclaimer, the term of this patent is extended or adjusted under 35 U.S.C. 154(b) by 160 days.

(21) Appl. No.: 10/148,889

(22) PCT Filed: Dec. 14, 2000

(86) PCT No.: PCT/SE00/02531
§ 371 (c)(1), (2), (4) Date: Jun. 17, 2002

(87) PCT Pub. No.: WO01/43670
PCT Pub. Date: Jun. 21, 2001

(65) Prior Publication Data
US 2002/0183660 A1 Dec. 5, 2002

(30) Foreign Application Priority Data
Dec. 16, 1999 (SE) .............................. 9904616

(51) Int. Cl.$^7$ ................................................ A61F 5/00
(52) U.S. Cl. .............................. 602/7; 602/6; 602/900; 623/901; 425/2; 264/222
(58) Field of Search ................... 623/33, 901; 602/6–7, 602/900; 425/2; 264/219, 222, 259, 271.1, 299, 313, 316, 319, 322, 403–404; 428/110; 219/212, 213, 549; 607/108, 98

(56) References Cited

U.S. PATENT DOCUMENTS

| | | | | |
|---|---|---|---|---|
| 1,498,655 A | * | 6/1924 | Hauptman | 219/549 |
| 2,185,692 A | * | 1/1940 | McCleary | 219/510 |
| 3,326,211 A | * | 6/1967 | Logue et al. | 602/7 |
| 3,467,086 A | * | 9/1969 | Addison et al. | 602/7 |
| 3,906,943 A | | 9/1975 | Arluck | 128/90 |
| 3,936,661 A | * | 2/1976 | Furuishi et al. | 219/528 |
| 4,019,505 A | * | 4/1977 | Wartman | 602/7 |
| 4,244,771 A | * | 1/1981 | Pierce | 156/499 |
| 4,821,708 A | * | 4/1989 | Guignard et al. | 602/7 |
| 4,932,852 A | * | 6/1990 | Suzuki | 425/2 |
| 5,016,624 A | * | 5/1991 | Garrett et al. | 602/7 |
| 5,690,880 A | * | 11/1997 | Le Coent | 264/257 |
| 6,676,618 B2 | * | 1/2004 | Andersen | 602/7 |
| 6,723,960 B2 | * | 4/2004 | DiMartino et al. | 219/386 |

* cited by examiner

Primary Examiner—Linda C. M. Dvorak
Assistant Examiner—Michael P. Straightiff
(74) Attorney, Agent, or Firm—Jacobson Holman PLLC

(57) ABSTRACT

The use of a flexible, foldable or rollable and heatable mat for the manufacture of an orthosis, in which a flat sheet of a thermoplastic material is heated on a flat-laid mat to a temperature at which the sheet softens and can be readily shaped, whereafter the sheet is applied to and shaped on part of a patient's body and then allowed to cool on the patient so as to form a supporting orthosis. The mat can be transported in a rolled-up state or a folded state and laid out on a supporting surface, such as a floor surface in the proximity of the patient. The mat includes a heating element disposed over the area of the mat and functioning to deliver heat uniformly to the sheet.

8 Claims, 1 Drawing Sheet

USE OF A HEATABLE MAT FOR MANUFACTURING AN ORTHOTIC DEVICE

This is a nationalization of PCT/SE00/02531 filed Dec. 14, 2000 and published in English.

BACKGROUND OF THE INVENTION

1. Field of the Invention

The present invention relates to the use of a heatable and flexible mat in the manufacture of an orthosis.

2. Description of the Related Art

It is well known to manufacture an orthosis, by heating a sheet of thermoplastic material to a temperature at which the sheet softens to a state in which it can be readily shaped, wherewith the warm and softened sheet can be applied to a relevant part of a patient's body and shaped to provide the support intended, whereafter the orthosis is allowed to cool and solidify to provide the intended support. The sheet of material may, of course, be cut to provide an orthosis of appropriate size, either before or after shaping the sheet.

An orthosis technician will often visit a patient, for example a hospital visit, with the intention of manufacturing an orthosis for the patient concerned. For instance, a patient may have a broken leg and the entire leg may be encased in plaster, whereafter having first established that the healing process has proceeded as desired, the doctor concerned will prescribe removal of the plaster and its replacement with an orthosis placed over the fracture region, so as to enable the patient to walk or move with mobility in his/her knee joint.

The orthosis technician will normally bring with him one or more sheets of varying sizes and shapes, and also of different thicknesses. The technician may also bring with him an industrial hot-air gun with which to soften the sheet, by blowing a stream of hot air thereon. This procedure is afflicted with several problems. One problem is that the power consumed by the electrically operated hot-air device in softening the sheet over the whole of its area is relatively high, in the order of 3,000 watts, which often results in a blown fuse, with well known drawbacks as a result. Furthermore, a hot-air gun is very noisy in operation. U.S. Pat. No. 3,906,943 describes softening of the orthosis sheet with a hot-air gun or a heating plate.

One problem with this solution is that the technician is not certain of how uniformly the sheet of material has been heated, meaning in practice that the sheet may have sub-areas which have not been softened to an extent that will enable the sheet to be shaped comfortably and correctly on the patient.

SUMMARY OF THE INVENTION

One object of the present invention is to teach a use of a heating sheet with which the problems associated with prior orthosis manufacture technology can be restricted or eliminated.

This object is achieved by the use of a flexible mat that can be stored and transported in a folded or rolled state and that includes a heating element which is disposed over the full area of the mat and which is adapted to emit heat uniformly over the area of the mat in conjunction with the manufacture of an orthosis. The mat is laid flat on a flat surface, such as on the floor in the proximity of the patients, and a flat sheet of thermoplastic material is placed on the thus laid mat and heated to a temperature at which the sheet softens and can be readily shaped. Thereafter the heated sheet is applied to and shaped on a part of a patient's body and then allowed to cool on thereon so as to form a supporting orthosis.

Further developments of the invention include use of a mat whose heating element is powered electrically using a cable that includes a power regulator. The power regulator can be controlled by a temperature sensor that detects the temperature of the mat surface in an area on which the sheet is heated.

It is known to heat and soften a thermoplastic sheet that is to form part of an orthosis with the aid of an underlay that can be heated over its surface, wherewith the plastic sheet is placed on the heated underlay and therewith heated to an extent that will enable the sheet to be readily shaped. In accordance with the present invention, there is used an underlay in the form of a flexible mat that can be stored and transported in a folded state, or preferably in a rolled-up state, and then lain out on a flat surface, normally the floor, at the place where the orthosis shall be produced, so as to minimise the transport distance and transport time for the heated and softened sheet between the heating underlay and the patient. Because the underlay is heated uniformly over the whole of its area, uniform heating of the sheet over the whole of its surface is ensured. The underlay may incorporate a temperature sensor which functions to control a power control device connected to a current supply conductor connected to a heating element disposed over the surface of the underlay. As a result of the uniform emission of heat over said area from the underlay to the sheet, the power required is minimised so as to enable the requisite underlay heating power to be kept well beneath 2,000 watts, at which a standard fuse serving an electric outlet will not normally blow.

The resistive electric heating element is disposed over and incorporated in a silicon rubber mat. The thermoplastic sheet from which the orthosis shall be produced may comprise thermoplastic resin, such as SUNSPLINT thermoplastic resin, for instance, such thermoplastic being one which can be shaped at a temperature of +70° C., for instance. When the plastic sheet is shaped on the patient, a protective cloth, such as a textile hose for instance, may first be applied to the patient prior to shaping the plastic sheet around the patient's contours.

A mat that can be used in the manufacture of an orthosis is shown schematically in the accompanying drawing.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
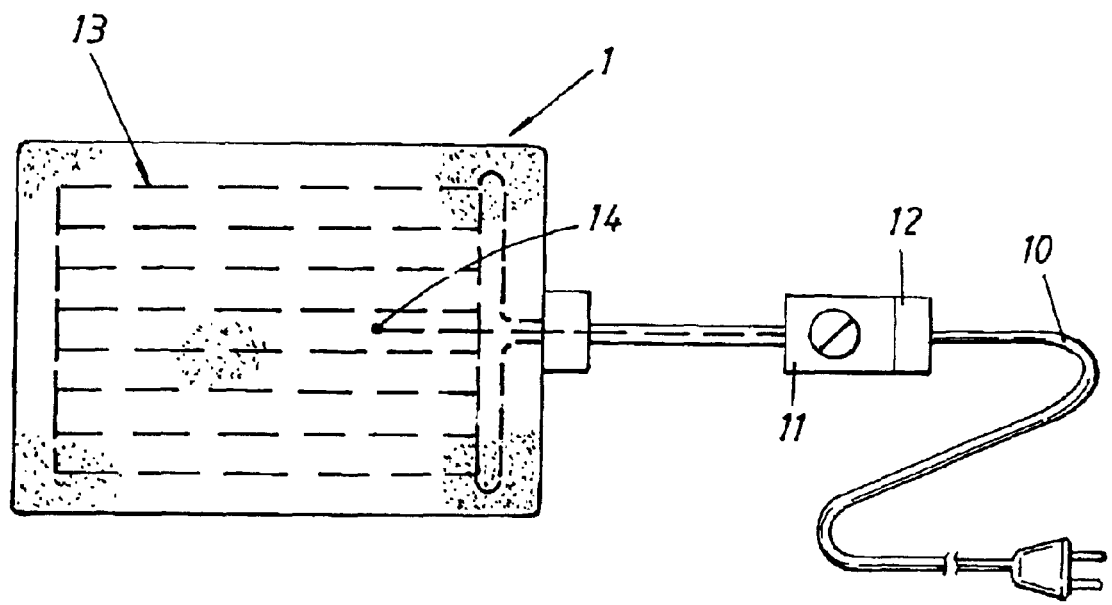
FIG. 1 is a plan view of a heating mat for heating a thermoplastic sheet.
Figure 2:
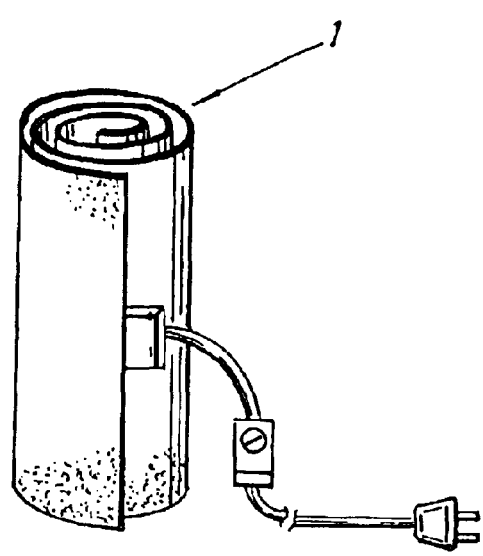
FIG. 2 shows the mat rolled-up.

FIG. 1 shows a rectangular silicone rubber mat 1 that has been laid flat and whose sides measure 65×90 cm. Although not shown in detail, a resistive electric heating element 13 is disposed essentially over the full area of the mat 1.

A power cable 10 that can be connected to the mains is coupled to the electric heating element via a power regulator 11. The power regulator may include an electric switch and/or an earth fault switch 12. The power regulator 11 may be controlled by a temperature sensor 14 mounted in the mat 1 primarily for detecting the temperature to which a thermoplastic sheet resting on the mat 1 has been heated so as to enable said sheet to be shaped into an orthosis. The temperature sensor 14 may be connected by a conductor to the power regulator 11, in order to control the regulator.

By producing the mat 1 from a flexible material that can be folded-up or rolled-up for storage and transporting purposes, the mat will only take-up a small amount of space during transportation and/or storage, while enabling the mat to be easily laid-out flat on a flat undersurface, such as a floor surface.

With regard to heating of the thermoplastic sheet, it may be beneficial to subject the sheet to a load that will cause the sheet to lie flat and in close abutment with the surface of the mat 1. A layer of heat insulation may be placed between the underside of the mat 1 and the underlying support surface, to restrict heat transfer to said surface. The heat insulating layer, for instance a flexible sheet of foamed neoprene, may be placed on one main surface of the mat 1.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of manufacturing an orthosis using a flexible mat that can be stored and transported in a folded or rolled state and that includes a heating element which is disposed over a full area of the mat and which emits heat uniformly over the area of the mat, comprising the steps of:

laying the mat flat on a flat surface;

placing a flat sheet of thermoplastic material on the thus laid mat and heating said sheet to a temperature at which said sheet softens and can be readily shaped; and applying the heated sheet to and shaping said sheet on a part of a patient's body and then allowing said sheet to cool on said patient so as to form a supporting orthosis.

2. The method according to claim 1, wherein the heating element of said mat is powered electrically via a cable that includes a power regulator.

3. The method according to claim 2, wherein the power regulator is controlled by a temperature sensor that detects a mat surface temperature in an area on which the sheet is heated.

4. The method according to claim 1, wherein the mat is laid flat on a floor surface.

5. A method of manufacturing an orthosis using a flexible mat that can be stored and transported in a folded or rolled state and that includes a heating element which emits heat uniformly over an area of the mat, the method comprising the steps of:

transporting said mat in the folded or rolled state to a patient;

unfolding or unrolling the mat to lay said mat on a generally flat surface and activating said heating element to heat said mat;

placing a flat sheet of thermoplastic material on the mat and heating said sheet through contact with said heated mat to a temperature at which said sheet softens and can be readily shaped; and applying the heated sheet to and shaping said sheet on a part of a patient's body and then allowing said sheet to cool on said patient so as to form a supporting orthosis.

6. The method according to claim 5, wherein the heating element of said mat is powered electrically via a cable that includes a power regulator.

7. The method according to claim 6, wherein the power regulator is controlled by a temperature sensor that detects a mat surface temperature in an area on which the sheet is heated.

8. The method according to claim 5, wherein the mat is laid flat on a floor surface.

* * * * *